(12) United States Patent
Kim et al.

(10) Patent No.: US 9,138,601 B2
(45) Date of Patent: Sep. 22, 2015

(54) METHOD OF IMPROVING SKIN REGENERATION EFFECT OF MEDICINAL MATERIALS BY DOUBLE BOILING USING EARTHENWARE POT

(75) Inventors: Dong Hyun Kim, Suwon-si (KR); Jun Seong Park, Suwon-si (KR); Hui Kyeung Chang, Yongin-si (KR); Duck Hee Kim, Seoul (KR); Han Kon Kim, Suwon-si (KR)

(73) Assignee: AMOREPACIFIC CORPORATION, Seoul (KR)

( * ) Notice: Subject to any disclaimer, the term of this patent is extended or adjusted under 35 U.S.C. 154(b) by 0 days.

(21) Appl. No.: 13/392,164

(22) PCT Filed: Aug. 18, 2010

(86) PCT No.: PCT/KR2010/005457
§ 371 (c)(1),
(2), (4) Date: Feb. 24, 2012

(87) PCT Pub. No.: WO2011/025176
PCT Pub. Date: Mar. 3, 2011

(65) Prior Publication Data
US 2012/0148686 A1 Jun. 14, 2012

(30) Foreign Application Priority Data

Aug. 31, 2009 (KR) ........................ 10-2009-0081142

(51) Int. Cl.
| | | |
|---|---|---|
| *A61K 36/00* | (2006.01) | |
| *A61K 36/25* | (2006.01) | |
| *A61K 36/288* | (2006.01) | |
| *A61K 36/232* | (2006.01) | |
| *A61K 36/8945* | (2006.01) | |
| *A61Q 19/00* | (2006.01) | |
| *A61K 8/97* | (2006.01) | |
| *A61K 36/258* | (2006.01) | |
| *A61K 36/71* | (2006.01) | |

(52) U.S. Cl.
CPC . *A61Q 19/00* (2013.01); *A61K 8/97* (2013.01); *A61K 36/232* (2013.01); *A61K 36/258* (2013.01); *A61K 36/288* (2013.01); *A61K 36/71* (2013.01); *A61K 36/8945* (2013.01); *A61K 2800/87* (2013.01)
USPC ............................ 424/725; 424/728; 424/764

(58) Field of Classification Search
None
See application file for complete search history.

(56) References Cited

U.S. PATENT DOCUMENTS 3,880,899 A * 4/1975 Marteau et al. .................. 554/11
5,009,891 A 4/1991 Niwa et al.

FOREIGN PATENT DOCUMENTS

| CN | 101366940 A | * | 2/2009 |
|---|---|---|---|
| JP | 50-88238 A | | 7/1975 |
| JP | 63-79834 A | | 4/1988 |
| JP | 7-61916 A | | 3/1995 |
| JP | 3023855 U | | 2/1996 |
| JP | 10-45615 A | | 2/1998 |
| JP | 2000-103718 A | | 4/2000 |
| JP | 2002-145616 A | | 5/2002 |
| JP | 2004-105934 A | | 4/2004 |
| JP | 2008-534614 A | | 8/2008 |
| JP | 2009-13086 A | | 1/2009 |
| JP | 2009-35494 A | | 2/2009 |
| KR | 2003030826 A | * | 4/2003 |
| KR | 2003089649 A | * | 11/2003 |
| KR | 2004105048 A | * | 12/2004 |
| KR | 647346 B1 | * | 11/2006 |
| KR | 2006132212 A | * | 12/2006 |
| WO | WO 2006/105450 A2 | | 10/2006 |

OTHER PUBLICATIONS

Han, Seung-Kwan, "Antioxidative Effect of Different Kinds of Propolis on the Oxidation of Edible Oils," *Korean J. Food Sci. Ani. Resour.*, 23(2):168-71 (2003).
Jo, et al., "Protective Effects of a Herb, *Artemisia capillaris*, Against Radiation-induced DNA Damage," *J Korean Soc Food Sci Nutr*, 33(1):22-27 (2004).
International Search Report for corresponding International Application No. PCT/KR2010/005457 (Form PCT/ISA/210).
Office Action for Chinese Patent Application No. 201080049134.2 mailed Dec. 25, 2012.
"How to Take Ginseng and what to be avoided when taking Ginseng", *Lauren Tiandi*, No. 6, p. 28 (Jun. 30, 2004).
Office Action for Japanese Patent Application No. 2012-526628 mailed Aug. 26, 2014.
Office Action for Chinese Patent Application No. 201080049134.2 mailed Jun. 28, 2012.
Wang, "The Making of Chinese Medicine", Amazingly Effective Prescriptions, *Beijing Science and Technology Publishing*, 1991, pp. 459-461.

* cited by examiner

*Primary Examiner* — Qiuwen Mi
(74) *Attorney, Agent, or Firm* — Merchant & Gould P.C.

(57) ABSTRACT

Disclosed is a method capable of improving the skin regeneration effect of medicinal materials through double boiling using an earthenware pot. The method shows an excellent skin regeneration effect, and the extract of medicinal materials obtained therethrough can be variously applied in the fields of cosmetics, health foods or medicine.

6 Claims, 2 Drawing Sheets

Fig.2

| Control | Concentrate obtained through double boiling using glass container | Concentrate obtained through double boiling using wood container | Concentrate obtained through double boiling using steel container | Concentrate obtained through double boiling using earthenware pot |

24 hours later 48 hours later

METHOD OF IMPROVING SKIN REGENERATION EFFECT OF MEDICINAL MATERIALS BY DOUBLE BOILING USING EARTHENWARE POT

This application is a U.S. National Stage Application under 35 U.S.C. §371 of International Patent Application No. PCT/KR2010/005457, filed 18 Aug. 2010, which claims the benefit of priority to Korean Patent Application No. 10-2009-0081142, filed 31 Aug. 2009, the disclosures of all of which are hereby incorporated by reference in their entireties. The International Application was published in Korean on 3 Mar. 2011 as WO 2011/025176. To the extent appropriate, a claim of priority is made to each of the above disclosed applications.

TECHNICAL FIELD

The present disclosure relates to method of improving the skin regeneration effect of medicinal materials through double boiling using an earthenware pot.

BACKGROUND

Human skin protects the human body from the external environment. When the skin is wounded, the process of wound healing begins as blood fills the wound site and the reduction of granules of platelets as well as the activation of the Hageman factor is initiated. Blood coagulation is a provisional defensive mechanism, protecting the exposed damaged tissues and allowing migration of cells during wound healing.

The classic model of wound healing is divided into four phases: inflammatory, reepithelization phase, proliferative and maturational. In the inflammatory phase, immune cells migrate to the wound site from the blood vessels. Then, growth factors and signaling molecules that induce the formation of granulation tissue are released. In the absence of severe infection, the inflammatory phase is usually short.

In the proliferative phase, granulation tissues are formed at the wound site similar to reepithelization phase. The granulation tissue is composed of fibroblasts and inflammatory cells as well as extracellular matrix components including immature collagen, fibronectin, hyaluronic acid, etc. It is important in wound healing that the granulation tissues quickly fill the wound site and form an organized structure. In the reepithelization phase, a new epidermis is formed and the epithelial layer is restored as the open wound is covered by a layer of keratinocytes. The cells begin to migrate from the wound edge or from the remaining dermis to the living connective tissue under a scab floating through the wound site.

When the reepithelization is completed, the wound area is reduced through a series of processes involving increase and construction of the connective tissue. In the maturational phase, coagulated cells of recovery phase and capillaries are removed gradually. If the tissues are formed excessively or are not degraded normally, scar will remain.

The general wound healing process is explained above. In wound healing, it is also important to treat the wound without side effects or scars as much as to treat it quickly. Accordingly, well-balanced filling of the tissue cells through inhibition of inflammation and control of growth factor expression is important and efforts are made to find materials having such activities.

Also, various efforts are made to extract active ingredients for wound healing from a variety of medicinal materials. Accordingly, a method allowing for more effective extraction of the active ingredients is required.

SUMMARY OF THE INVENTION

Technical Problem

The present disclosure is directed to providing a method capable of improving the skin regeneration effect of medicinal materials.

Technical Solution

In one general aspect, the present disclosure provides a method based on double boiling using an earthenware pot.

Advantageous Effects

The method of improving the skin regeneration effect of medicinal materials according to the present disclosure provides a superior skin regeneration effect.

BRIEF DESCRIPTION OF THE DRAWINGS

FIG. 2 compares the skin regeneration effect of a concentrate obtained through double boiling using containers of different materials respectively measured by in vitro wound healing assay.

DETAILED DESCRIPTION

Figure 1:
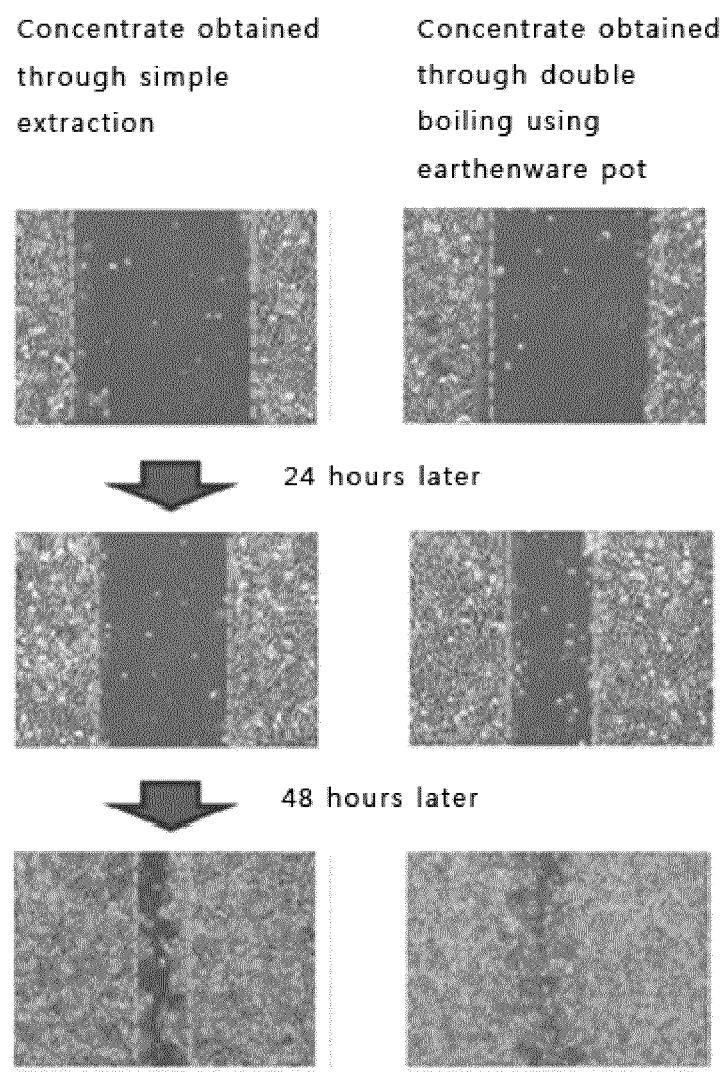
FIG. 1 compares the skin regeneration effect of a concentrate obtained through double boiling using an earthenware pot and a concentrate obtained through simple extraction.

The present disclosure provides a method of improving the skin regeneration effect of medicinal materials through double boiling using an earthenware pot. Double boiling using an earthenware pot is remarkably superior in improving the skin regeneration effect of medicinal materials to double boiling using containers made of other materials. Through repeated diverse experiments, the inventors of the present disclosure have confirmed that the extract of medicinal materials prepared through double boiling using an earthenware pot have excellent skin regeneration effect.

As used herein, the term "double boiling using an earthenware pot" means boiling medicinal materials through double boiling using an earthenware pot. For example, an earthenware pot holding medicinal materials may be heated after being immersed in a heating vessel containing water to a height of about ⅔.

As used herein, the term "earthenware pot" collectively refers to unglazed and glazed earthenware pots. Traditionally, the earthenware pot has been used to store seasoning, staple food, subsidiary food, beverage, etc. and for fermentation of alcoholic beverages. The earthenware pot is made as follows. First, earth is kneaded, dried slightly in the shade, and then hit with a mullet into a shape of a brick. Then, it is prepared into a slab by hitting on the ground. The slab is shaped into a pot on a wheel using a club. The shape of the earthenware pot is determined by the wheel speed, handicraft of the potter, or the like.

The medicinal material used in the method of improving the skin regeneration effect of medicinal materials according to the present disclosure is not particularly limited and may include animal materials, herbs or medicinal materials used in the Oriental medicine. Examples of the medicinal material include *Schisandra chinensis*, sweet flag, jujube, longan, biota, *Scutellaria baicalensis*, radish seed, asparagus, lilyturf, white atractylodes rhizome, peony root, licorice, *Taraxacum mongoiicum*, Chinese yam, nelumbinis semen, castaneae semen, coix seed, ephedra, Chinese matrimony vine, cornelian cherry, thrumwort, peony root bark, *Araliae continnentalis* radix, psyllium, ginseng, deer antlers, grape root, steamed rehmannia root, rehmannia root, dried rehmannia root, platycodon root, zingiberis rhizoma, tangerine peel, rhubarb, *Angelica dahurica, Ostericum koreanum, Angelica tenuissima, Crataegus pinnatifida, Asarum sieboldii, Bupleurum falcaturn, Cyperus rotundus, Dendranthema indicum, Cimicifuga heracleifolia, Astragalus membranaceus, Gardenia jasminoides, Areca catech*, etc., but are not limited thereto. In an exemplary embodiment, the medicinal material used in the method of improving the skin regeneration effect of medicinal materials may be one or more selected from a group consisting of ginseng, *Taraxacum mongoiicum, Angelica tenuissima*, Chinese yam and *Cimicifuga heracleifolia*. The medicinal material may be in the natural form as picked or in the dried form of chop, powder, paste, dumpling or extract.

In an exemplary embodiment, the double boiling may be performed at temperatures of 20-180° C. The method of improving the skin regeneration effect of medicinal materials according to the present disclosure is applicable to the medicinal materials that are effectively extracted at low temperatures as well as those extracted at high temperatures. For example, the double boiling may be performed at high temperatures of 80-150° C., more specifically 90-130° C. Also, the double boiling may be performed at low temperatures of 30-70° C., more specifically 40-60° C.

In an exemplary embodiment, the double boiling may be performed at pressures of 0.5-5.0 atm. The method of improving the skin regeneration effect of medicinal materials according to the present disclosure is applicable to the medicinal materials that are effectively extracted at low pressures as well as those extracted at high pressures. For example, the double boiling may be performed at low pressures of 0.6-0.9 atm. Also, the double boiling may be performed at high pressures of 1.5-5.0 atm.

The method of improving the skin regeneration effect of medicinal materials according to the present disclosure is applicable at various temperatures and pressures. For example, the double boiling of the medicinal material may be performed under the condition of high temperature and high pressure or under the condition of low temperature and low pressure. The double boiling condition may be different depending on the kind, type, properties, etc. of the medicinal material. In an exemplary embodiment, the double boiling may be performed at 80-150° C. and 1.5-5.0 atm. In an exemplary embodiment, the double boiling may be performed at 30-70° C. and 0.6-0.9 atm.

A method for preparing an extract of medicinal materials using the method of improving the skin regeneration effect of medicinal materials according to the present disclosure is not particularly limited. It may comprise repeated processes of double boiling and cooling. For example, the method of improving the skin regeneration effect of medicinal materials may comprise: (a) double boiling the medicinal materials for 60-80 hours; (b) cooling at room temperature for 12-36 hours; (c) double boiling in water for 12-36 hours; (d) filtering the medicinal materials; and (e) concentrating the resulting extract.

More specifically, the method of improving the skin regeneration effect of medicinal materials may comprise: (a) double boiling the medicinal materials for 72 hours; (b) cooling at room temperature for 24 hours; (c) double boiling in water for 24 hours; (d) filtering the medicinal materials; and (e) concentrating the resulting extract.

In an exemplary embodiment, the double boiling may be performed using water heated in a cauldron. The water heated in a cauldron maintains constant temperature and is not easily cooled down in response to the temperature change of the surrounding environment.

MODE FOR INVENTION

The examples and experiments will now be described. The following examples and experiments are for illustrative purposes only and not intended to limit the scope of this disclosure.

Example 1

Preparation of Concentrate Through Double Boiling Using Earthenware Pot

Ginseng, *Taraxacum mongoiicum, Angelica tenuissima*, Chinese yam and *Cimicifuga heracleifolia* (1 kg each) were added to an earthenware pot together with water (10 L) and double boiled for 72 hours using a cauldron. After cooling for 24 hours at room temperature, double boiling was further performed for 24 hours in water. After filtering the remaining medicinal materials, the filtrate was concentrated under reduced pressure to obtain a concentrate (50 g).

Comparative Example 1

Preparation of Concentrate Through Simple Extraction

Ginseng, *Taraxacum mongoiicum, Angelica tenuissima*, Chinese yam and *Cimicifuga heracleifolia* (1 kg each) were added to an earthenware pot together with water (10 L) and heated for 72 hours. After cooling for 24 hours at room temperature, the earthenware pot was further heated for 24 hours by directly heating not by double boiling. After filtering the remaining medicinal materials, the filtrate was concentrated under reduced pressure to obtain a concentrate (40 g).

Comparative Example 2

Preparation of Concentrate Through Double Boiling Using Glass Container

Ginseng, *Taraxacum mongoiicum, Angelica tenuissima*, Chinese yam and *Cimicifuga heracleifolia* (1 kg each) were added to a glass container together with water (10 L) and double boiled for 72 hours using a cauldron. After cooling for 24 hours at room temperature, double boiling was further performed for 24 hours in water. After filtering the remaining medicinal materials, the filtrate was concentrated under reduced pressure to obtain a concentrate (65 g).

Comparative Example 3

Preparation of Concentrate Through Double Boiling Using Wood Container

Ginseng, *Taraxacum mongoiicum, Angelica tenuissima*, Chinese yam and *Cimicifuga heracleifolia* (1 kg each) were added to a wood (cedar) container together with water (10 L) and double boiled for 72 hours using a cauldron. After cooling for 24 hours at room temperature, double boiling was further performed for 24 hours in water. After filtering the remaining medicinal materials, the filtrate was concentrated under reduced pressure to obtain a concentrate (45 g).

Comparative Example 4

Preparation of Concentrate Through Double Boiling Using Steel Container

Ginseng, *Taraxacum mongoiicum, Angelica tenuissima*, Chinese yam and *Cimicifuga heracleifolia* (1 kg each) were added to a steel container together with water (10 L) and double boiled for 72 hours using a cauldron. After cooling for 24 hours at room temperature, double boiling was further performed for 24 hours in water. After filtering the remaining medicinal materials, the filtrate was concentrated under reduced pressure to obtain a concentrate (55 g).

Test Example 1

Activation of Skin Regenerating Cells by Concentrate of Medicinal Materials Through Visual Form Human keratinocytes (HaCaT) were acquired from the Korean Cell Line Bank (Seoul, Korea). The HaCaT cells were cultured in an animal cell incubator under the condition of 37° C. and 5% $CO_2$ using Dulbecco's modified Eagle's medium (DMEM) containing 10% (v/v) fetal bovine serum (FBS), 100 U/mL penicillin and 100 µg/mL streptomycin. $1.5 \times 10^6$ HaCaT cells were transferred to each well of a culture plate. After a single layer of the cells was formed, "scratch damage" was induced using a p200 pipette tip.

A concentrate was prepared by double boiling using an earthenware pot (Example 1) or by simple extraction without double boiling (Comparative Example 1). The "scratch damaged" cells treated with each concentrate was at 10 ppm. While culturing the cells, the extent of regeneration of the scratch damage was observed 24 hours and 48 hours later. The result is shown in FIG. 1.

As seen from FIG. 1, the "scratch damage" of the cells treated with the concentrate prepared by double boiling using an earthenware pot (Example 1) showed remarkably decreased area of scratch damage with time. The speed of wound healing was much faster than that for the concentrate prepared by simple extraction (Comparative Example 1).

Also, the result of comparing the skin regeneration effect after treating the cells with the concentrate prepared by double boiling using an earthenware pot (Example 1) and concentrates prepared by double boiling using different containers (Comparative Examples 2-4) is shown in FIG. 2. In the figure, control shows the result for the cells not treated with the concentrate of the medicinal materials and others show the result for the cells treated with the concentrates prepared by double boiling using different containers (Comparative Examples 2-4). The result is shown in FIG. 2.

As seen from FIG. 2, the skin regeneration effect was better when the cells were treated with the concentrate prepared by double boiling using an earthenware pot than when they were treated with the concentrates prepared by double boiling using glass, wood or steel container.

INDUSTRIAL APPLICABILITY

The method of improving the skin regeneration effect of medicinal materials according to the present disclosure shows an excellent skin regeneration effect, and the extract of medicinal materials obtained therethrough can be variously applied in the fields of cosmetics, health foods or medicine.

We claim:

1. A method of increasing an inherent effect of a medicinal material, comprising double boiling a medicinal material using an earthenware pot, wherein the double boiling using an earthenware pot is a boiling process in which the earthenware pot is heated after being immersed in a heating vessel containing water; wherein the medicinal material comprises ginseng, *Taraxacum mongolicum, Angelica tenuissima*, Chinese yam and *Cimicifuga heracleifolia*; and wherein the inherent effect of the medicinal material is a skin regeneration effect.

2. The method of claim 1, wherein the double boiling is performed at temperatures of 20-180° C.

3. The method of claim 1, wherein the double boiling is performed at pressures of 0.5-5.0 atm.

4. The method of claim 1, wherein the double boiling is performed at temperatures of 80-150° C. and at pressures of 1.5-5.0 atm.

5. The method of claim 1, wherein the double boiling is performed at temperatures of 30-70° C. and at pressures of 0.6-0.9 atm.

6. The method of claim 1, which comprises:
double boiling the medicinal materials for 60-80 hours;
cooling at room temperature for 12-36 hours;
double boiling in water for 12-36 hours;
filtering the medicinal materials; and
concentrating the resulting extract.

* * * * *